(12) United States Patent
Kawamura et al.

(10) Patent No.: US 8,485,018 B2
(45) Date of Patent: Jul. 16, 2013

(54) METHOD OF DETERMINING FALLING STATE OF FALLING BODY FOR VISCOMETER OF FALLING BODY TYPE, FALLING-BODY VELOCITY MEASURING SENSOR, AND VISCOMETER OF FALLING BODY TYPE INCLUDING SAME

(75) Inventors: Kimito Kawamura, Moriya (JP); Motoyuki Tagashira, Moriya (JP); Eiji Tamura, Amagasaki (JP)

(73) Assignee: Asahi Group Holdings, Ltd., Sumida-ku, Tokyo (JP)

( * ) Notice: Subject to any disclaimer, the term of this patent is extended or adjusted under 35 U.S.C. 154(b) by 0 days.

(21) Appl. No.: 13/499,565

(22) PCT Filed: May 21, 2010

(86) PCT No.: PCT/JP2010/003425
§ 371 (c)(1),
(2), (4) Date: Mar. 30, 2012

(87) PCT Pub. No.: WO2011/039906
PCT Pub. Date: Apr. 7, 2011

(65) Prior Publication Data
US 2012/0186326 A1    Jul. 26, 2012

(30) Foreign Application Priority Data
Oct. 3, 2009 (JP) ................................ 2009-231050

(51) Int. Cl.
*G01M 7/00*    (2006.01)
(52) U.S. Cl.
USPC ........................................ 73/12.01

(58) Field of Classification Search
USPC .............................................. 73/12.01–12.13
See application file for complete search history.

(56) References Cited

U.S. PATENT DOCUMENTS

| | | | | |
|---|---|---|---|---|
| 3,512,396 A | * | 5/1970 | Okamoto | 73/54.21 |
| 3,717,026 A | * | 2/1973 | Ito | 73/54.21 |

(Continued)

FOREIGN PATENT DOCUMENTS

| | | |
|---|---|---|
| JP | 48-56480 | 8/1973 |
| JP | 63-97845 | 6/1988 |

(Continued)

OTHER PUBLICATIONS

International Search Report for PCT Application No. PCT/JP2010/003425, Japanese Patent Office, dated Aug. 17, 2010, 5 pages.

*Primary Examiner* — Lisa Caputo
*Assistant Examiner* — Octavia Davis-Hollington
(74) *Attorney, Agent, or Firm* — Sterne, Kessler, Goldstein & Fox P.L.L.C.

(57) ABSTRACT

A technique used to determine a falling state of a falling body, such as whether the falling body reaches a falling termination speed and falls uniformly or falls with a change in the speed is provided. In particular, a method of determining a falling state of a falling body passing through a measured substance inserted into a measuring container is provided, the method including: measuring a first elapsed time which is a time interval between extreme values of two potentials generated in a first coil pair when the falling body passes through the first coil pair and a second elapsed time which is a time interval between extreme values of two potentials generated in a second coil pair when the falling body passes through the second coil pair; and determining the falling state of the falling body by comparing the first elapsed time with the second elapsed time.

6 Claims, 13 Drawing Sheets

| U.S. PATENT DOCUMENTS | | | | |
|---|---|---|---|---|
| 3,772,910 A * | 11/1973 | McGinn et al. | | 73/54.19 |
| 4,388,823 A * | 6/1983 | Garnaud et al. | | 73/54.18 |
| 4,627,272 A * | 12/1986 | Wright | | 73/54.23 |
| 5,327,778 A * | 7/1994 | Park | | 73/54.21 |
| 2011/0174061 A1* | 7/2011 | Kawamura et al. | | 73/54.02 |

FOREIGN PATENT DOCUMENTS

| JP | 5-39424 | 6/1993 |
|---|---|---|
| JP | 08-219973 | 8/1996 |
| JP | 2006-208260 | 8/2006 |

* cited by examiner

METHOD OF DETERMINING FALLING STATE OF FALLING BODY FOR VISCOMETER OF FALLING BODY TYPE, FALLING-BODY VELOCITY MEASURING SENSOR, AND VISCOMETER OF FALLING BODY TYPE INCLUDING SAME

BACKGROUND OF THE INVENTION

1. Technical Field

The present invention relates to a falling body viscometer which measures the falling speed of a falling body falling inside a measured substance in a measuring container and measures the falling speed of the measured substance from the measurement value, and more particularly, a technique of determining the falling state of the falling body.

2. Background Art

For example, Patent Literature 1 has a configuration in which a substantially needle-like falling body is dropped into a tubular measuring container, which is particularly designed to measure the viscosity of blood. More specifically, a pair of electromagnetic induction sensors which are vertically separated from each other are attached to a tubular measuring container. The time from the time point when receiving a detecting signal for the substantially needle-like falling body from the upper electromagnetic induction sensor to the time point when receiving a detecting signal for the substantially needle-like falling body from the lower electromagnetic induction sensor is measured. Then, a falling termination speed is detected based on the time and the distance between the upper and lower electromagnetic induction sensors.

Further, as disclosed in Patent Literatures 1 and 2, the "falling termination speed" indicates a falling speed when the falling body falls uniformly inside the fluid. The speed obtained by the electromagnetic induction sensor is regarded as the "falling termination speed", and the viscosity is calculated by using the falling termination speed.

With the assumption that the falling speed of the falling body reaches the falling termination speed (in which the falling body falls uniformly inside the fluid), the viscosity of the liquid as the measuring target is calculated.

PATENT LITERATURE

Patent Literature 1: Japanese Patent Application Laid-Open (JP-A) No. 2006-208260
Patent Literature 2: JP-A No. 8-219973

SUMMARY OF INVENTION

Technical Problem

The falling body described above may not reach the falling termination speed and may not fall uniformly inside the fluid depending on the measuring object because the distance or the time at which the falling body reaches the upper electromagnetic induction sensor after the falling body starts to fall may be short.

In such a case, the method of measuring (calculating) the viscosity on the assumption that the falling body falls uniformly, the measurement result (the calculation result) is not sufficiently reliable.

Therefore, it is an object of the invention to provide a technique that is helpful for determining the falling state of the falling body such as determining whether a falling body reaches a falling termination speed and falls uniformly or determining whether a falling body falls with a change in speed.

Solution to Problem

The problem to be solved by the invention has been described above, and the means for solving the problem will be described below.

In one embodiment, there is provided a method of determining a falling state of a falling body passing through a measured substance inserted into a measuring container by using a falling speed measuring sensor including a first coil pair which includes a pair of coils disposed in the outer periphery of the measuring container and separated from each other in the vertical direction and a second coil pair which includes a pair of coils disposed in the outer periphery of the measuring container, separated from each other in the vertical direction, and disposed below the first coil pair so as to be separated therefrom by a specified distance, the method including: measuring a first elapsed time which is a time interval between extreme values of two potentials generated in the first coil pair when the falling body passes through the first coil pair and a second elapsed time which is a time interval between extreme values of two potentials generated in the second coil pair when the falling body passes through the second coil pair; and determining the falling state of the falling body by comparing the first elapsed time with the second elapsed time.

In one embodiment, there is provided a falling speed measuring sensor which measures a falling speed of a falling body passing through a measured substance inserted into a measuring container, the falling speed measuring sensor including: a first coil pair which includes a pair of coils disposed in the outer periphery of the measuring container and separated from each other in the vertical direction; and a second coil pair which includes a pair of coils disposed in the outer periphery of the measuring container, separated from each other in the vertical direction, and disposed below the first coil pair so as to be separated therefrom by a specified distance, wherein the falling speed measuring sensor is able to perform an operation of measuring a first elapsed time which is a time interval between extreme values of two potentials generated in the first coil pair when the falling body passes through the first coil pair and a second elapsed time which is a time interval between extreme values of two potentials generated in the second coil pair when the falling body passes through the second coil pair, and determining the falling state of the falling body by comparing the first elapsed time with the second elapsed time.

In one embodiment, there is provided a falling body viscometer including: the falling speed measuring sensor described above.

In one embodiment, there is provided a method of determining a falling state of a falling body passing through a measured substance inserted into a measuring container by using a falling speed measuring sensor including a first coil pair which includes a pair of coils disposed in the outer periphery of the measuring container and separated from each other in the vertical direction and a second coil pair which includes a pair of coils disposed in the outer periphery of the measuring container, separated from each other in the vertical direction, and disposed below the first coil pair so as to be separated therefrom by a specified distance, the method including: measuring a first elapsed time which is a time interval between extreme values of two potentials generated in the first coil pair when the falling body passes through the first coil pair and a second elapsed time which is a time interval between extreme values of two potentials generated in the second coil pair when the falling body passes through the second coil pair; and determining the falling state of the falling body in a manner such that a falling speed which is obtained by dividing the vertical center distance of the first coil pair by the first elapsed time is compared with a falling speed which is obtained by dividing the vertical center distance of the second coil pair by the second elapsed time.

In one embodiment, there is provided a falling speed measuring sensor which measures a falling speed of a falling body passing through a measured substance inserted into a measuring container, the falling speed measuring sensor including: a first coil pair which includes a pair of coils disposed in the outer periphery of the measuring container and separated from each other in the vertical direction; and a second coil pair which includes a pair of coils disposed in the outer periphery of the measuring container, separated from each other in the vertical direction, and disposed below the first coil pair so as to be separated therefrom by a specified distance, wherein the falling speed measuring sensor is able to perform an operation of measuring a first elapsed time which is a time interval between extreme values of two potentials generated in the first coil pair when the falling body passes through the first coil pair and a second elapsed time which is a time interval between extreme values of two potentials generated in the second coil pair when the falling body passes through the second coil pair and determining the falling state of the falling body in a manner such that a falling speed which is obtained by dividing the vertical center distance of the first coil pair by the first elapsed time is compared with a falling speed which is obtained by dividing the vertical center distance of the second coil pair by the second elapsed time.

In one embodiment there is provided a falling body viscometer including: the falling speed measuring sensor described above.

Advantageous Effects of Invention

One effect of the invention is that it is possible to usefully determine the falling state of the falling body, such as whether the falling body falls uniformly, falls with an increase in the speed, or falls with a decrease in the speed.

DESCRIPTION OF EMBODIMENTS

Figure 1:
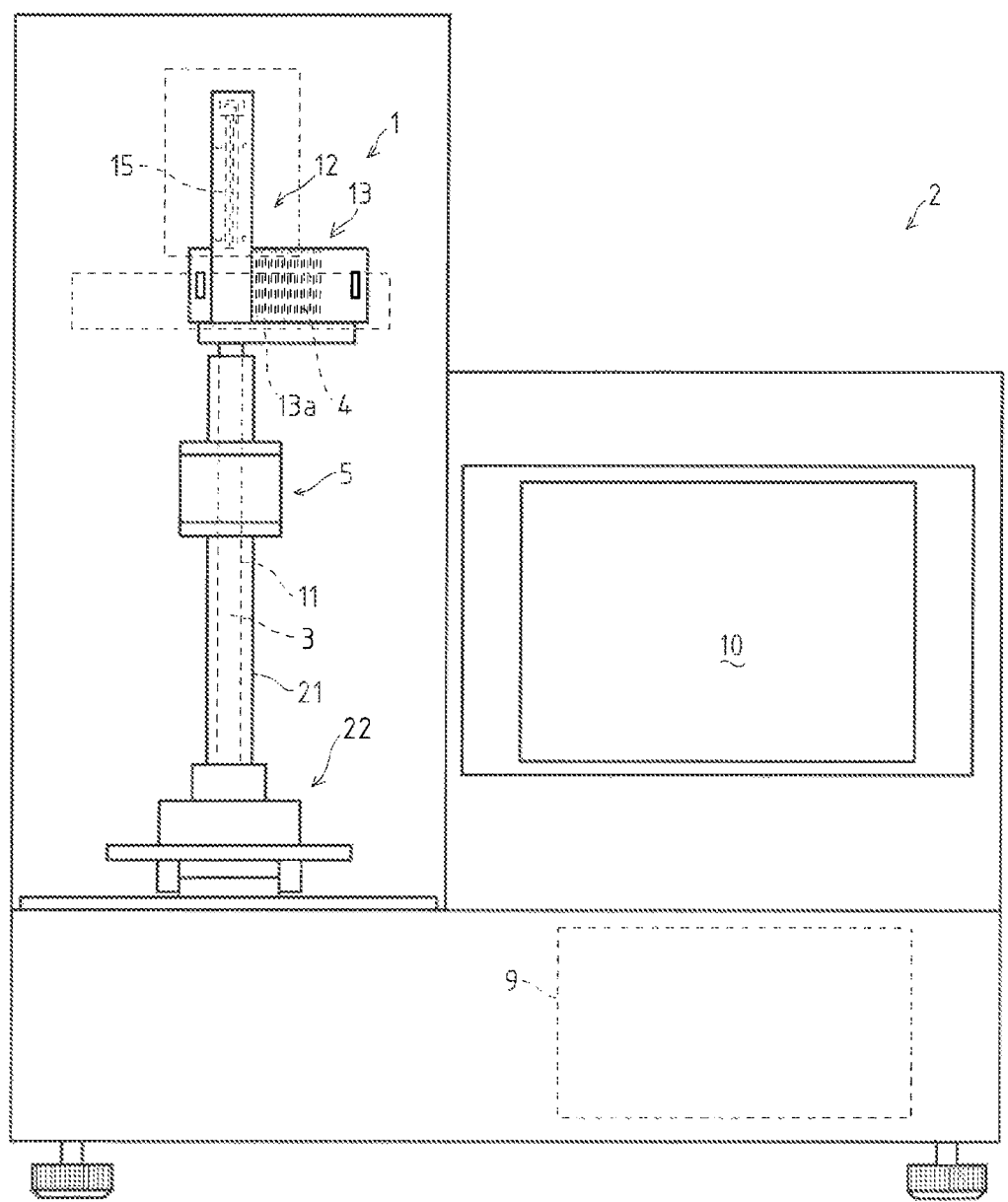
FIG. 1 is diagram illustrating a configuration of a falling body viscometer which includes a falling body sending apparatus.
Figure 10:
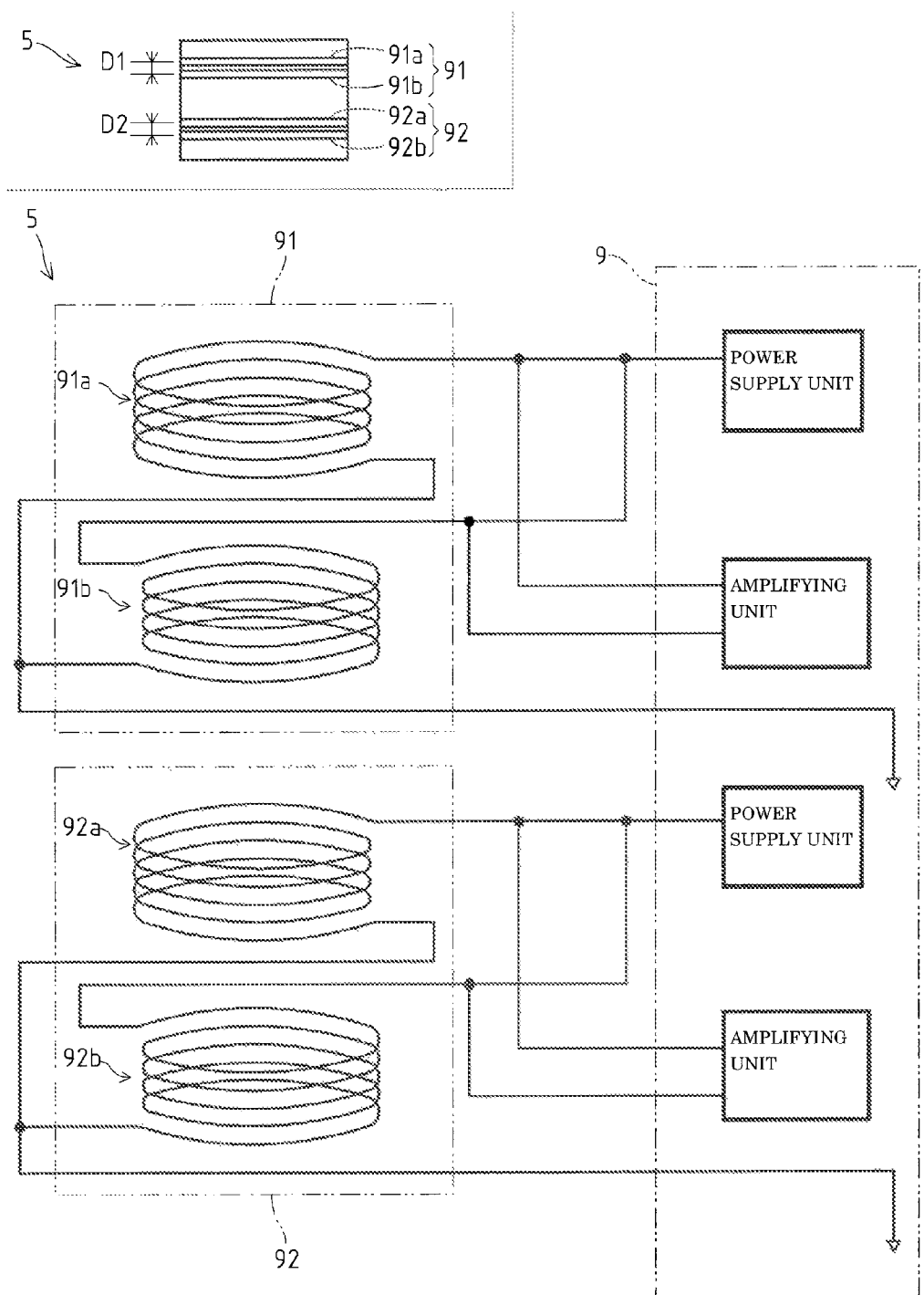
FIG. 10 is a diagram illustrating a configuration example of a falling speed measuring sensor.
Figure 11:
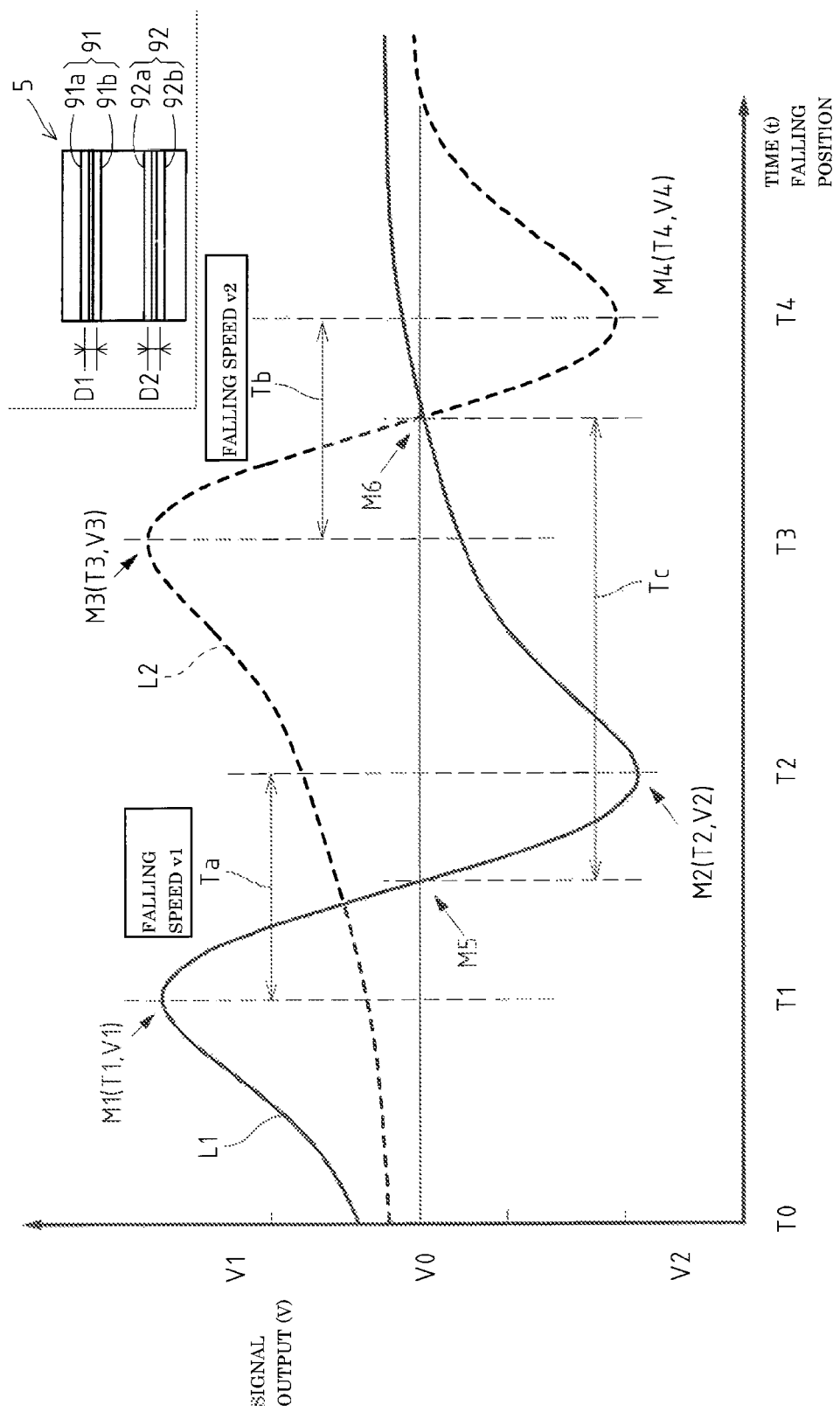
FIG. 11 is a diagram illustrating a waveform of a change in the potential detected by the falling speed measuring sensor.

As illustrated in FIGS. 1, 10, and 11, an embodiment of the invention provides a method of determining a falling state of a falling body 4 passing through a measured substance 3 inserted into a measuring container 11 by using a falling speed measuring sensor 5 including a first coil pair 91 that includes a pair of coils 91a and 91b disposed in the outer periphery of the measuring container 11 and separated from each other in the vertical direction and a second coil pair 92 that includes a pair of coils 92a and 92b disposed in the outer periphery of the measuring container 11, separated from each other in the vertical direction, and disposed below the first coil pair 91 so as to be separated therefrom by a specified distance, the method including: measuring a first elapsed time Ta that is a time interval between extreme values M1 and M2 of two potentials generated in the first coil pair 91 when the falling body 4 passes through the first coil pair 91 and a second elapsed time Tb that is a time interval between extreme values M3 and M4 of two potentials generated in the second coil pair 92 when the falling body 4 passes through the second coil pair 92; and determining the falling state of the falling body 4 by comparing the first elapsed time Ta with the second elapsed time Tb.

Accordingly, it is possible to determine the falling state of the falling body 4, such as whether the falling body 4 falls uniformly, falls with an increase in speed, or falls with a decrease in speed.

FIG. 1 illustrates the configuration of the falling body viscometer 2 which includes the falling body sending apparatus 1 according to the embodiment of the invention. In the falling body viscometer 2, the substantially needle-like falling body 4 falls inside the measured substance 3 inserted into the measuring container 11, the falling speed of the falling body 4 is measured by the falling speed measuring sensor 5, and the viscosity of the measured substance 3 is measured by using the measured falling speed.

Further, as illustrated in FIG. 1, the falling body viscometer 2 includes an operation-display device 10 which displays the measured falling speed or viscosity or numerical values necessary for measurement thereon. Further, the measurement result may be output by printing from an output device (not illustrated).

Furthermore, the falling speed of the falling body 4 mentioned in the embodiment indicates the speed (the falling termination speed) when the falling body 4 uniformly falls (performs a uniform falling movement) inside the measured substance. Further, various examples of the measured substance 3 corresponding to a viscosity measuring object include blood, beverages, paint, chemicals, yeast, yogurt, mayonnaise, a resin, and the like through which the falling body 4 may fall by its own weight, and also include a Newtonian fluid and a non-Newtonian fluid.

Further, with regard to a method of calculating the viscosity using the measured falling speed, the method disclosed in JP-A No. 8-219973 or JP-A No. 2006-208260 may be used, and when the methods disclosed in these publications are executed by a program, the viscosity may be calculated.

<Apparatus Configuration>

Figure 2:
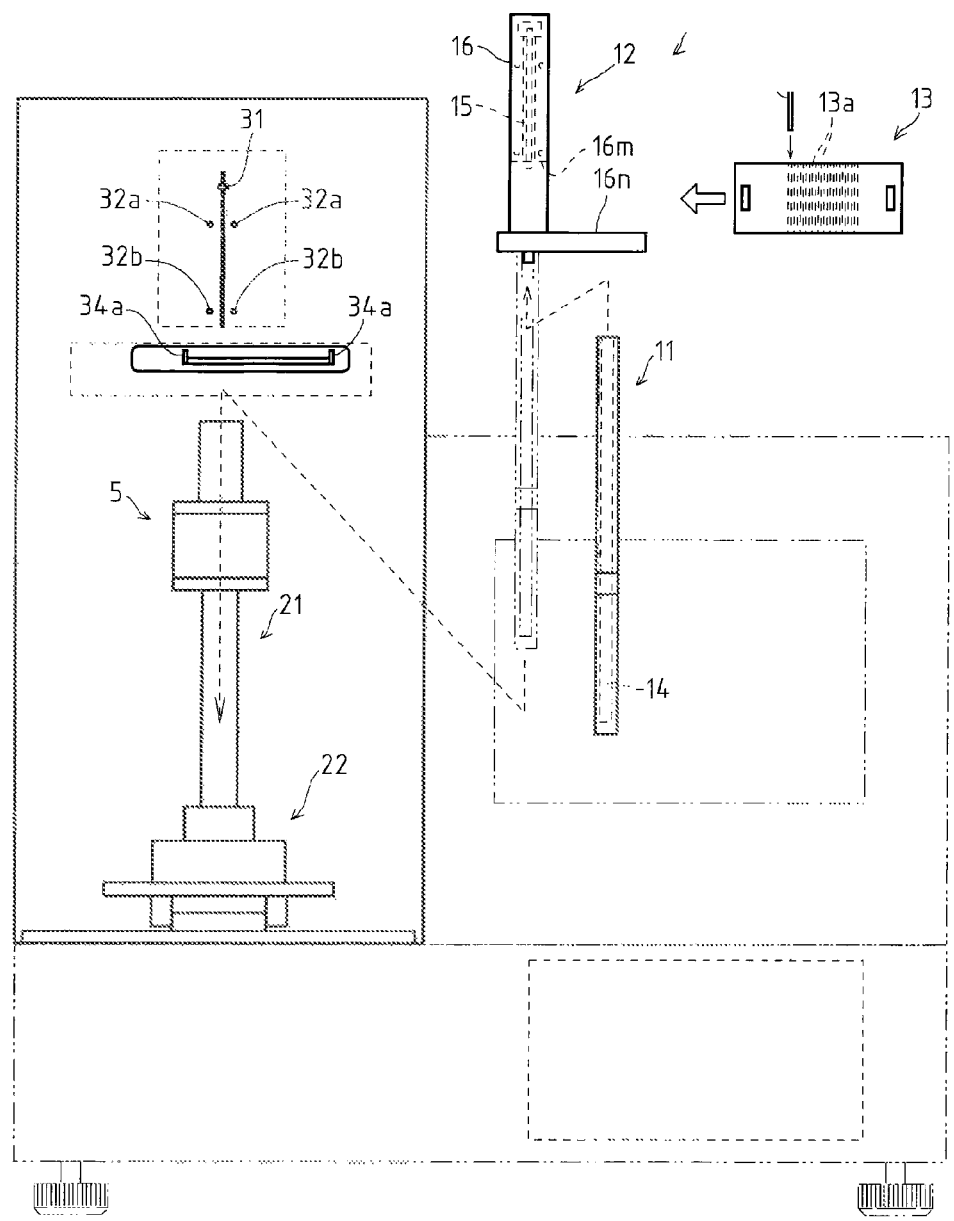
FIG. 2 is a diagram illustrating a state prior to assembly of the falling body viscometer.
Figure 3:
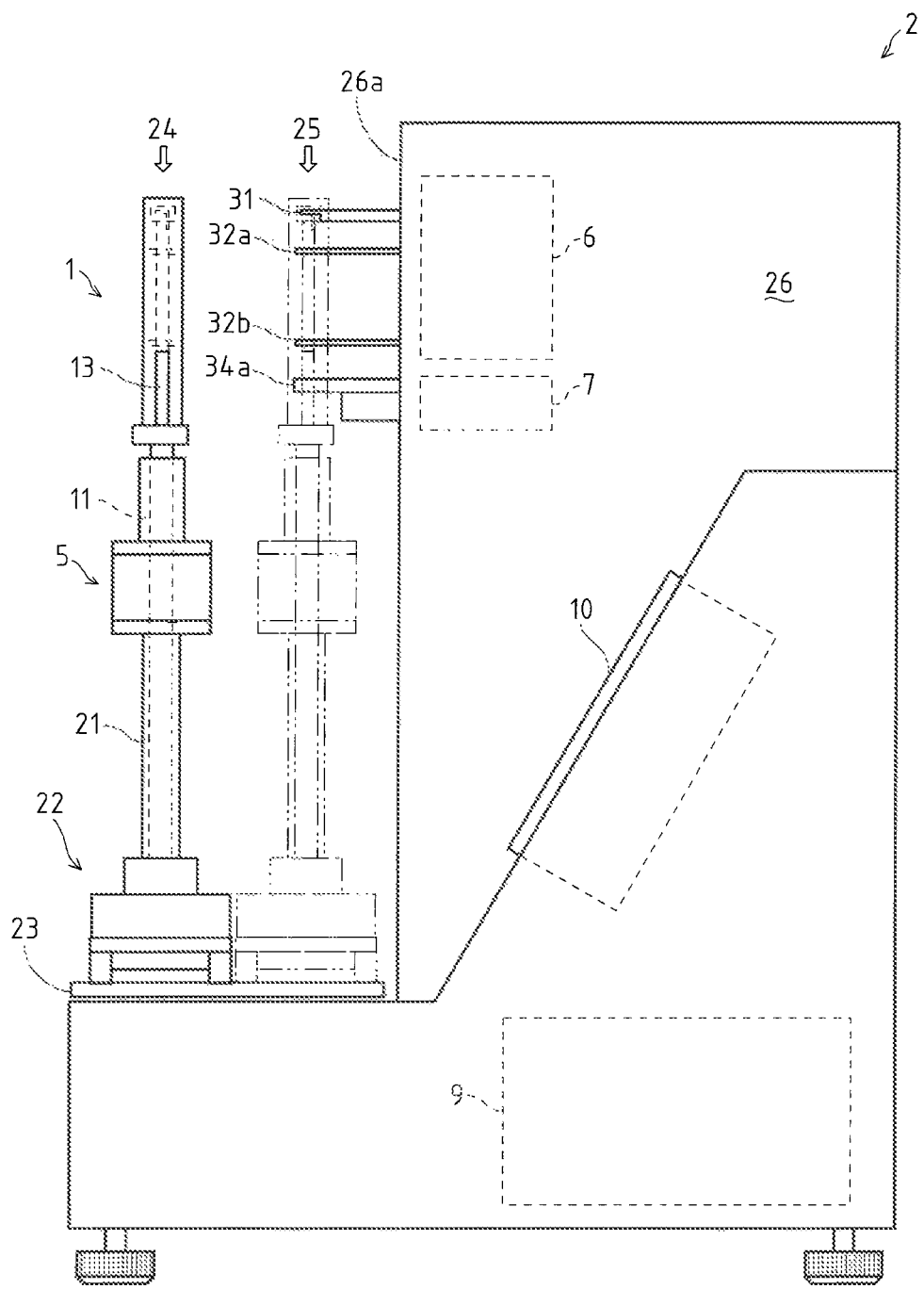
FIG. 3 is a side view illustrating an appearance of the falling body viscometer.

FIG. 1 is a front view illustrating the appearance of the falling body viscometer 2, FIG. 2 is a diagram illustrating a state prior to assembly of the falling body viscometer 2, and FIG. 3 is a side view illustrating the appearance of the falling body viscometer 2.

As illustrated in FIG. 1, the falling body viscometer 2 is provided with a moving table 22 where an outer cylinder 21 through which the measuring container 11 is inserted is uprightly installed. Further, the outer cylinder 21 is provided with the falling speed measuring sensor 5 which includes two coil pairs.

Further, as illustrated in FIG. 1, the falling body viscometer 2 is provided with an arithmetic and control unit 9, and the arithmetic and control unit 9 performs the automatic control (the execution of the time chart (FIG. 9)) for allowing the falling body to sequentially fall, the calculation of the falling speed or the viscosity, and the input and output of various information items with respect to the operation-display device 10.

Further, as illustrated in FIG. 2, the falling body sending apparatus 1 includes an extruding device 12 which is provided with the measuring container 11 inserted into the outer cylinder 21 from the upside thereof and the loading holder 13 which is installed in the extruding device 12 so as to be slidable in the transverse direction and be relatively movable.

Further, as illustrated in FIG. 2, the extruding device 12 is provided with the extruding pin 15 which is movable in the vertical direction, and the falling body 4 loaded in the loading holder 13 is sent into the measuring container 11 attached to the lower portion of the extruding device 12 by the extruding pin 15.

Further, as illustrated in FIG. 2, the measuring container 11 is a bottom tubular container, and the measured substance is inserted from the injection port formed in the upper portion thereof. Further, a falling body collecting unit 14 is formed in the lower portion of the measuring container 11, and the falling body which falls inside the measured substance is collected in the falling body collecting unit 14.

Further, as illustrated in FIG. 2, the loading holder 13 is formed as a block-like member which is long in the transverse direction, and plural porous loading units 13a are formed in the vertical direction. The substantially needle-like falling bodies 4 are respectively mounted on the respective loading units 13a Further, the loading holder 13 is inserted into a transverse sliding hole 16m formed in a pillar portion 16 of the extruding device 12, and is configured to move on a base member 16n forming the lower portion of the pillar portion 16 in the transverse direction.

Then, as illustrated in FIG. 2, the falling body sending apparatus 1 is assembled in a manner such that the extruding device 12 is attached by inserting the measured substance into the measuring container 11 and the loading holder 13 is set in the extruding device 12. Then, the falling body sending apparatus 1 is set in the outer cylinder 21 in a manner such that the portion of the measuring container 11 is inserted into the outer cylinder 21 from the upside thereof.

Furthermore, as illustrated in FIG. 2, because the loading holder 13 is detachable from the extruding device 12, the loading holder 13 having plural falling bodies 4 set therein may be prepared as a stock (as a cartridge type), and the next measuring work may be promptly performed by the replacement of the loading holder 13, which Obtains excellent workability.

Further, as illustrated in FIG. 3, the moving table 22 in which the outer cylinder 21 is uprightly formed is configured to be slidable in the depth direction of the measuring table 23 (the direction perpendicular to the Sliding direction of the loading holder 13), and may be set to a measurement escape position 24 corresponding to a front position and a measurement position 25 corresponding to the position for measurement. Then, at the measurement escape position 24, as illustrated in FIG. 2, a preparing work is performed so that the measuring container 11 which is attached to the falling body sending apparatus 1 is inserted into the outer cylinder 21. Then, in a state where the preparing work is completed, as illustrated in FIG. 3, the moving table 22 may be moved to the inward measurement position 25. Further, when the moving table 22 is moved to the measurement escape position 24 again after the measurement ends, the falling body sending apparatus 1 (the measuring container 11) may be extracted from the outer cylinder 21.

Further, as illustrated in FIG. 3, the falling body viscometer 2 is provided with a box portion 26 which accommodates the driving devices 6 and 7 and is long in the vertical direction, and a vertical moving arm 31, positioning pins 32a and 32b, and horizontal moving arms 34a protrude from a vertical wall portion 26a of the box portion 26. Furthermore, as illustrated in FIG. 2, the positioning pins 32a and 32b are provided at four positions in total, and the horizontal moving arms 34a are provided at two positions in total.

Figure 4:
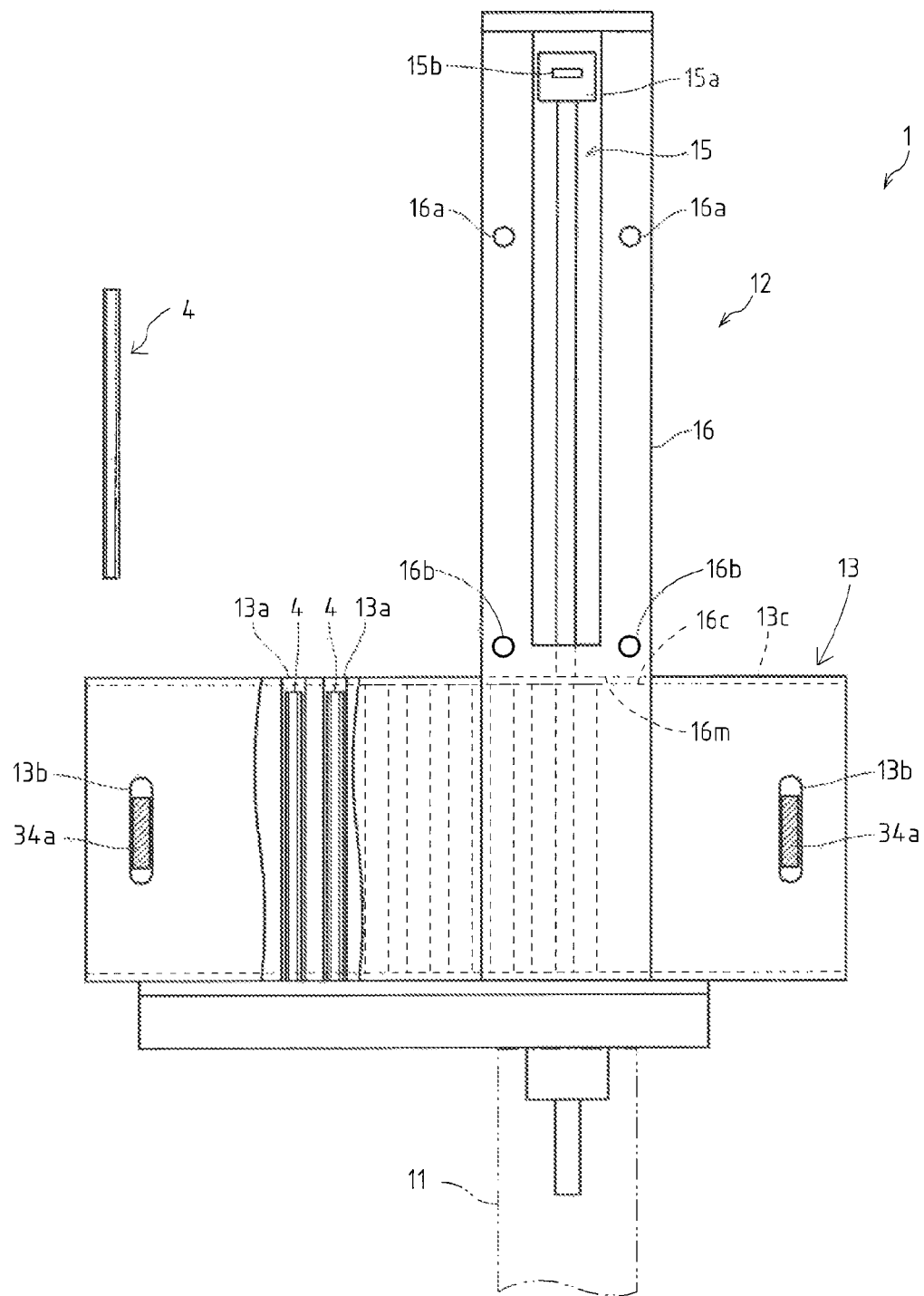
FIG. 4 is a bottom view illustrating a configuration of an extruding device of the falling body sending apparatus.

Further, as illustrated in FIG. 4, in the extruding device 12, the extruding pin 15 is configured to be movable inside the pillar-like pillar portion 16 in the vertical direction. The rear surface of the pillar portion 16 is provided with positioning holes 16a and 16b into which the positioning pins 32a and 32b illustrated in FIG. 3 are inserted and which are formed in the depth direction.

Further, as illustrated in FIG. 4, a connecting portion 15a which is formed in the upper portion of the extruding pin 15 is provided with a pin inserting hole 15b into which the front end portion of the vertical moving arm 31 illustrated in FIG. 3 is inserted and which is formed in the depth direction.

Further, as illustrated in FIG. 4, penetration holes 13b and 13b are formed at two positions on the left and right sides of the loading holder 13 the depth direction so that the horizontal moving arms 34a illustrated in FIG. 3 are inserted thereinto.

Then, with the configuration illustrated in FIG. 4, when the moving table 22 is moved from the measurement escape position 24 illustrated in FIG. 3 to the measurement position 25, the vertical moving arm 31 is inserted into the pin inserting hole 15b, the positioning pins 32a and 32b are respectively inserted into the positioning holes 16a and 16b, and the horizontal moving arms 34a and 34a are respectively inserted into the penetration holes 13b and 13b. Accordingly, when the moving table 22 is set in the measurement position 25 illustrated in FIG. 3, the relative position of each portion of the falling body sending apparatus 1 with respect to the box portion 26 (the vertical wall portion 26a) may be set to a specified position.

Further, as illustrated in FIG. 4, the falling bodies 4 are loaded in the respective loading units 13a of the loading holder 13. When the falling body 4 is pressed by the extruding pin 15 from the upside, the falling body 4 is sent into the measuring container 11. Further, the position where the movement of the extruding pin 15 stops may be specified by the driving device 6 (see FIG. 3) or the stopper (not illustrated) to be described later.

Figure 5:
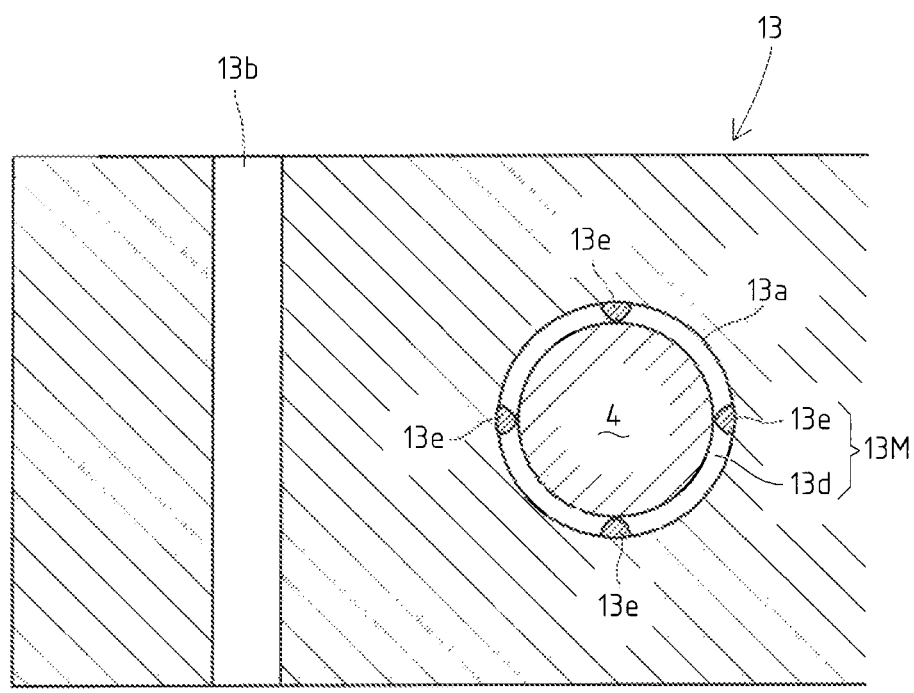
FIG. 5 is a cross-sectional view illustrating a loading unit of a loading holder.

Further, FIG. 5 illustrates the horizontal cross-sectional shape of the loading unit 13a of the loading holder 13, and the loading unit 13a includes the vertical hole 13d and the protrusions 13e protruding toward the axis of the vertical hole 13d. Then, when the protrusions 13e come into contact with the outer peripheral surface of the falling body 4, a frictional force is generated between the outer peripheral surface of the falling body 4 and the protrusions 13e. The falling body 4 does not naturally fall from the vertical hole 13d due to the frictional force, and is held in the loading unit 13a by the protrusions 13e.

Accordingly, as illustrated in FIG. 5, the loading unit 13a of the loading holder 13 includes the falling body holding mechanism 13M which allows the falling body 4 to be movable with respect to the loading unit 13a by the extruding device 12 (see FIG. 4) while holding the falling body 4 in the loading unit 13a. Further, in the falling body holding mechanism 13M, the loading unit 13a includes the vertical hole 13d and the protrusions 13e formed in the inner peripheral surface of the vertical hole 13d, and the falling of the falling body 4 is suppressed by the frictional force which is generated between the protrusions 13e and the peripheral surface of the falling body 4.

Further, according to the configuration illustrated in FIG. 5, because the respective falling bodies 4 are held by the appropriate frictional force obtained by the combination of the vertical hole 13d and the protrusions 13e which are formed in the inner surface of the loading unit 13a of the loading holder 13, the extruding device 12 (see FIG. 4) does not need an excessive load, and the falling body 4 does not fall freely. Accordingly, it is possible to reduce a work burden or reduce a variation in the measurement result with a simple structure.

Furthermore, in FIG. 5, the protrusions 13e are vertically long protrusions each having a substantially triangular cross-section are disposed at four positions, but the shape and the number thereof is not limited to the embodiment of FIG. 5. For example, a convex protrusion which has a tubular shape in the plan view may be provided in the end portion of the vertical hole 13d, a semi-spherical protrusion may be provided in the inner peripheral surface of the vertical hole 13d, or an internal tooth may be formed by forming a continuous uneven portion in the inner peripheral surface of the vertical hole 13d. Further, with regard to the protrusions 13e, the loading holder 13 may be formed of separate rubber or resin and may be formed at the same time when the vertical hole 13d is molded.

Then, as described above, because the falling body 4 is pressed by the extruding pin 15 so as to be sent out, the position where the falling body starts to freely fall (the position of the vertical direction) may be made to be uniform, a variation in time from the start of the free fall to the arrival at the falling speed measuring sensor 5 (see FIG. 1) may be suppressed, and a variation in the speed when the falling body passes through the falling speed measuring sensor 5 may be suppressed.

Figure 6:
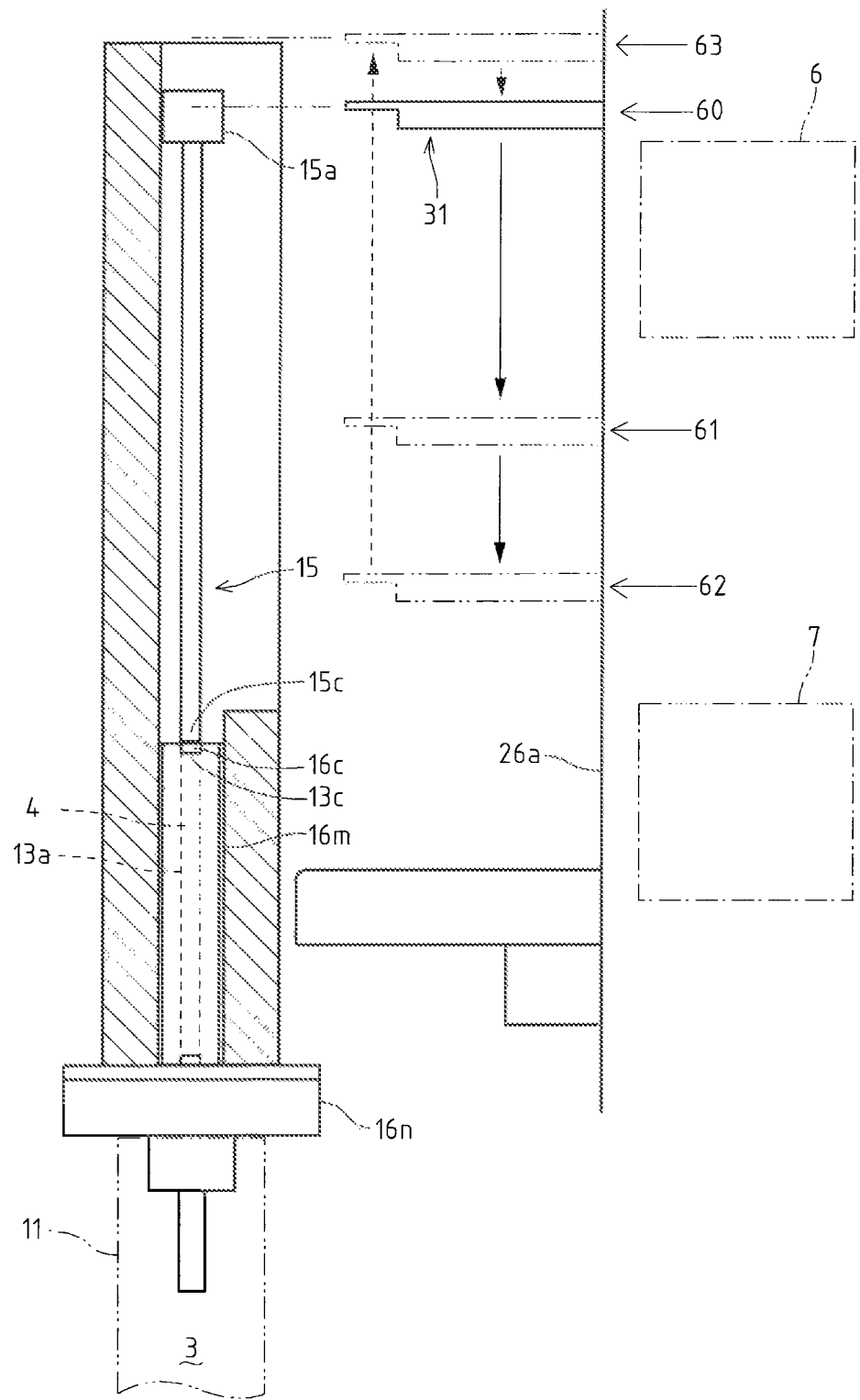
FIG. 6 is a side view illustrating a configuration of the extruding device of the falling body sending apparatus.

Further, as illustrated in FIGS. 4 and 6, because the vertical moving arm 31 is inserted into the connecting portion 15a which is provided in the upper portion of the extruding pin 15, the extruding pin 15 and the vertical moving arm 31 are connected to each other. Further, the vertical moving arm 31 is configured to move up and down by the driving device 6, so that the extruding pin 15 moves up and down along with the vertical moving arm 31. Then, when the vertical moving arm 31 moves downward, the falling body 4 is pressed by the extruding pin 15, so that the falling body 4 is sent out from the loading unit 13a and is sent into the measuring container 11. Furthermore, a configuration different from the configuration in which the pin inserting hole 15b and the vertical moving arm 31 are connected to each other as illustrated in FIGS. 4 and 6 may be used. For example, the upper portion of the extruding pin is pressed from the upside in the vertical moving arm so as to press the extruding pin, and after the falling body is sent out, the extruding pin is returned to an origin position (a position where the extruding pin is not pressed yet) by the returning force of an elastic member such as a spring.

In this way, because the driving device 6 operates the extruding pin 15, an operation of sending the falling body 4 may be automatically performed, and the workability of the measuring work may be improved. Furthermore, it is desirable that the driving device 6 is formed as a servo motor or a stepping motor in order to precisely control the timing at which the vertical moving arm 31 is moved or to precisely control the vertical position of the vertical moving arm 31.

Further, as illustrated in FIGS. 4 and 6, because the horizontal moving arms 34a are inserted into the penetration holes 13b of the loading holder 13, the horizontal moving arms 34a and the loading holder 13 are connected to each other. Further, the horizontal moving arms 34a are configured to move left and right by the driving device 7, so that the loading holder 13 moves left and right along with the horizontal moving arms 34a.

Then, as illustrated in FIGS. 4 and 6, the horizontal moving arms 34a are configured to sequentially move by a specified distance so that the respective loading units 13a of the loading holder 13 are sequentially disposed below the extruding pin 15 during the measurement. Further, the loading holder 13 is moved when the vertical moving arm 31 is disposed at an origin position 60 or an upper limit position 63 and the movement thereof is performed when the extruding pin 15 is not inserted into the loading unit 13a. Further, after the respective falling bodies 4 are completely sent out by the extruding pin 15, the horizontal moving arms 34a return to the original position, so that the loading holder 13 is also returned to the standby position (the state of FIG. 1) before the measurement.

Further, as illustrated in FIGS. 4 and 6, in the sliding hole 16m which is provided in the pillar portion 16 of the extruding device 12, a guide convex portion 16c protrudes downward, and the guide convex portion 16c is inserted into a guide groove 13c formed in the loading holder 13. Accordingly, the loading holder 13 is configured to move left and right by the guide convex portion 16c.

As described above, because the driving device 7 operates the loading holder 13, the loading holder 13 may be automatically sent out, and the workability of the measuring work may be improved. Furthermore, it is desirable that the driving device 7 is formed as a servo motor or a stepping motor in order to precisely control the timing at which the horizontal moving arms 34a are moved or to precisely control the horizontal position of moving arms 34a. Further, because the driving device 6 and the driving device 7 are synchronized in the arithmetic and control unit 9 (see FIG. 1), the timings of the horizontal movement of the loading holder 13 and the vertical movement of the extruding pin 15 are controlled, so that the falling bodies 4 may sequentially fall automatically.

Figure 7:
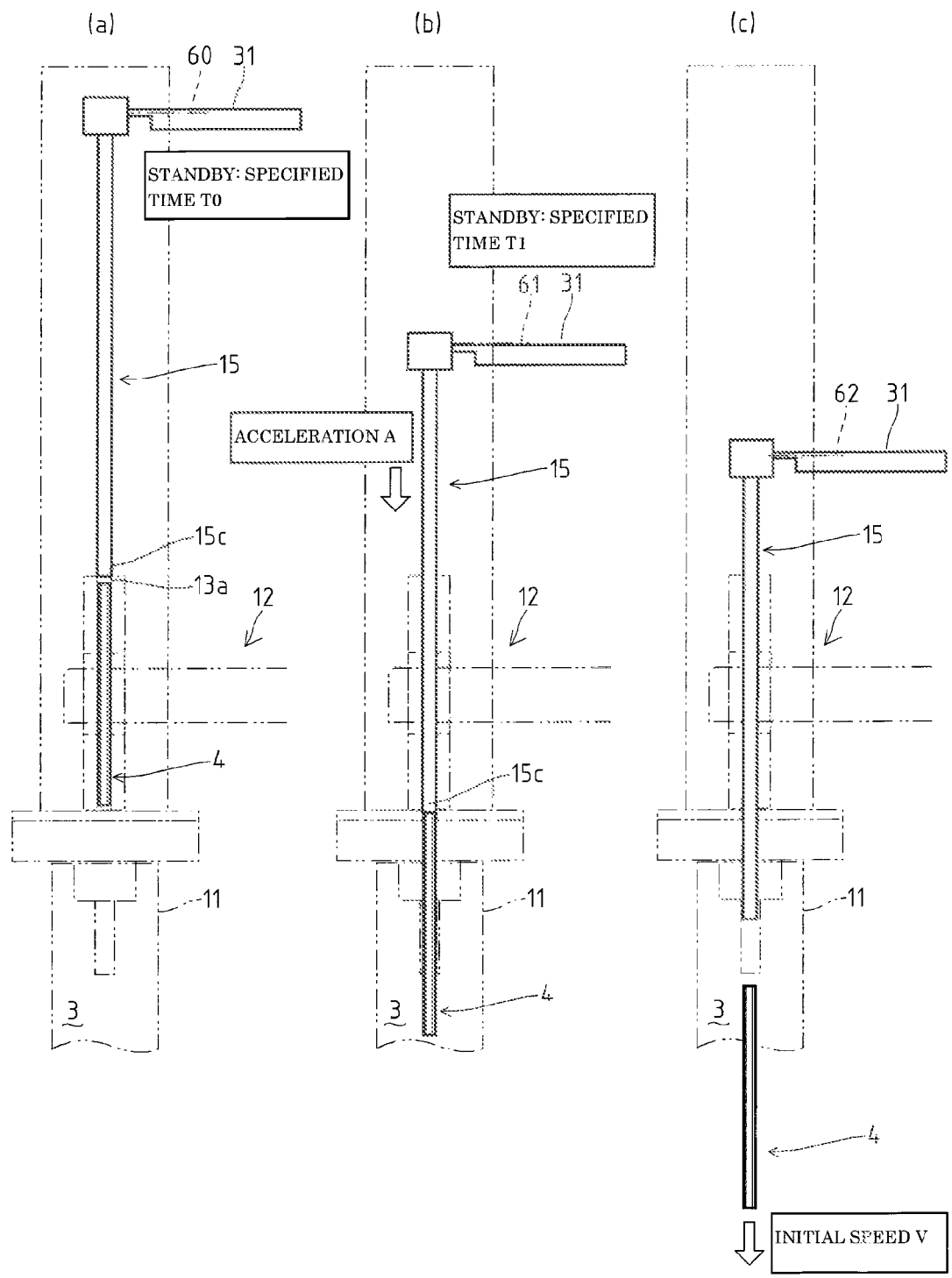
FIG. 7(a) is a diagram illustrating a state where a vertical moving arm is disposed at an origin position.
FIG. 7(b) is a diagram illustrating a state where the vertical moving arm is disposed at a first stop position.
FIG. 7(c) is a diagram illustrating a state where the vertical moving arm is disposed at a second stop position.

Further, as illustrated in FIGS. 6 and 7, the vertical moving arm 31 is controlled by the driving device 6 so that it is stopped at the origin position 60, the first stop position 61, the second stop position 62, and the upper limit position 63 (see FIG. 6) which are four positions in total.

Here, when the vertical moving arm 31 is disposed at the origin position 60, the lower end 15c of the extruding pin 15 is disposed above the loading unit 13a of the loading holder 13 when the connecting portion 15a of the upper portion of the extruding pin 15 is disposed at the above positions.

Further, when the vertical moving arm 31 moves down from the origin position 60 to the first stop position 61, the lower end 15c of the extruding pin 15 is inserted into the loading unit 13a so as to come into contact with the upper end portion of the falling body 4, and the falling body 4 moves downward. Here, the falling body 4 does not fall inside the measuring container 11, and is set to a standby state where a part (the lower portion) of the falling body 4 enters the measuring container 11 (the standby state where the lower portion protrudes downward from the extruding device 12).

Further, when the vertical moving arm 31 moves downward from the first stop position 61 to the second stop position 62, the extruding pin 15 further moves downward, and the falling body 4 falls inside the measuring container 11. Subsequently, the vertical moving arm 31 moves upward from the second stop position 62 to the upper limit position 63, and is returned to the origin position 60.

Further, as illustrated in FIGS. 6 and 7, the vertical moving arm 31 moves from the origin position 60 (FIG. 7(a)) to the first stop position 61 (FIG. 7(b)), and the movement thereof is stopped for a specified time T1. After the specified time T1, is elapsed, the movement from the first stop position 61 to the second stop position 62 (FIG. 7(c)) is started. That is, the falling of the falling body 4 may be delayed by the specified time T1.

Figure 8:
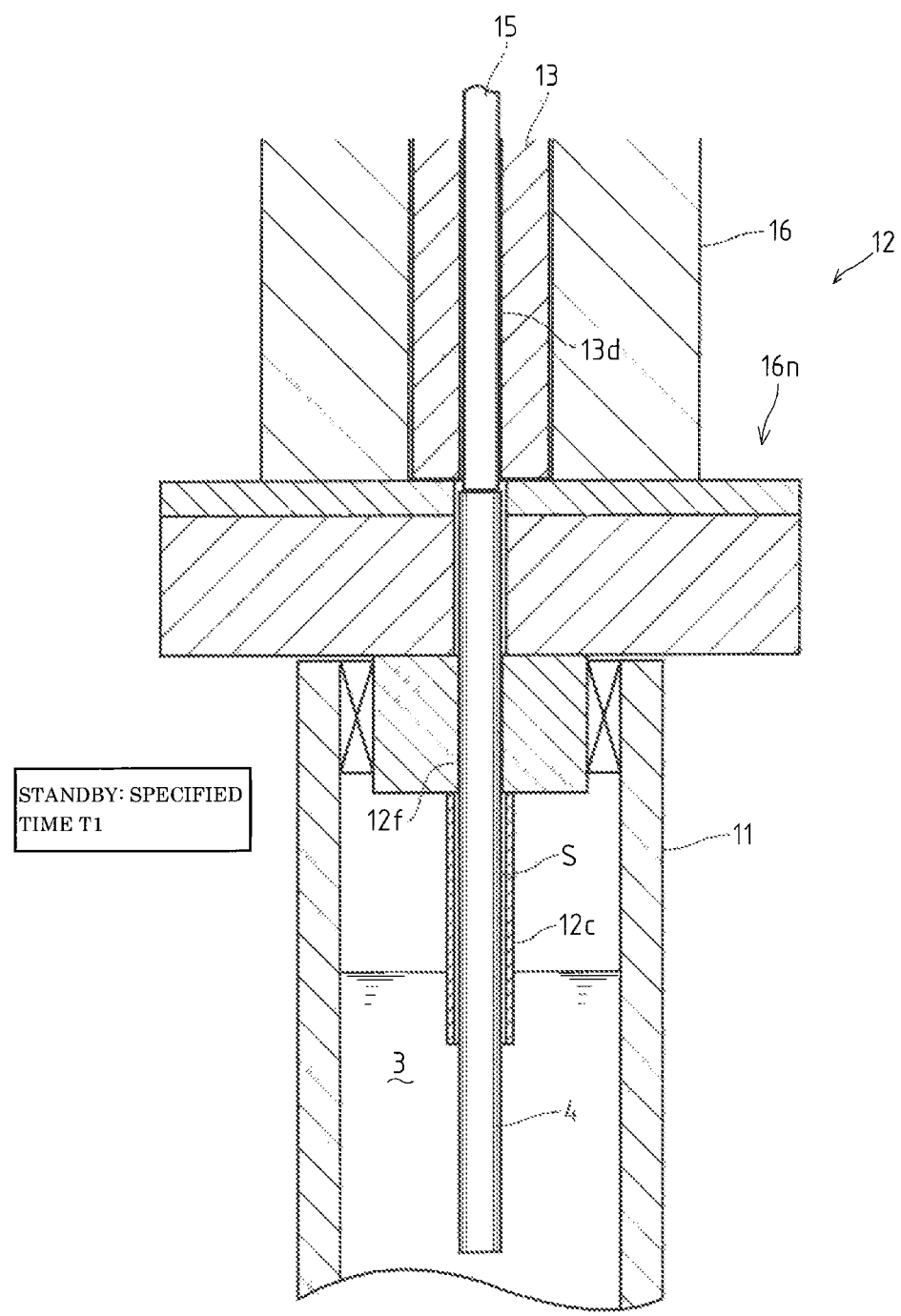
FIG. 8 is a diagram illustrating a state where the falling of the falling body is made to be in a standby state.

FIG. 8 illustrates a state where the falling of the falling body 4 is delayed by the specified time T1

In the lower portion of the base member 16n of the extruding device 12, a tubular guide portion 12c, which guides the falling body 4, protrudes therefrom, and when the guide portion 12c passes therethrough, the falling body 4 falls vertically. Then, in this configuration, in the falling standby state, the lower portion of the falling body 4 protrudes from the guide portion 12e, and at the protruding portion, the measured substance 3 infiltrates into the surface of the falling body 4.

Furthermore, because the measured substance 3 rises in a gap S which is formed between the guide portion 12c and the falling body 4 due to a so-called capillary phenomenon, the wide range in the surface of the falling body 4 infiltrates into the measured substance 3. In this way, because the measured substance 3 infiltrates into the surface of the falling body 4 before the falling of the falling body 4, it is possible to reduce a fluid frictional force which is generated between the falling body 4 and the measured substance 3 when the falling body 4 starts to fall, and to allow the falling body 4 to reliably fall uniformly (reach the terminal falling speed) within a limited falling distance inside the measuring container 11.

Furthermore, in the configuration illustrated in FIG. 8, the specified time T1 at which the falling of the falling body 4 is delayed when the vertical moving arm is disposed at the first stop position may be, for example, several seconds such as two seconds or three seconds and may be appropriately specified depending on the type of the measured substance 3 or the length of the falling body 4. Accordingly, it is possible to set a degree in which the measured substance 3 infiltrates into the surface of the falling body 4 and to allow the falling body 4 to reliably fall uniformly (reach the terminal falling speed) within a limited falling distance inside the measuring container 11. Furthermore, in order to delay the falling of the falling body 4 at that position, a vertical hole 12f which has a function of suppressing the falling of the falling body 4 by the frictional force with respect to the peripheral surface of the falling body is formed above the guide portion 12c in the base member 16n. The vertical hole 12f may be realized by forming the protrusions 13e illustrated in FIG. 5 as in the vertical hole 13d of the loading unit 13a of the loading holder 13.

Further, as illustrated in FIG. 7, the Vertical moving arm 31 moves with the specified acceleration A from the first stop position 61 (FIG. 7(b)) to the second stop position 62 (FIG. 7(c)), so that the falling body 4 is made to have an initial speed V and is sent into the measured substance 3. The operating speed of the vertical moving arm 31, that is, the operating speed of the extruding pin 15 may be set in advance according to the measured substance 3. Then, because the falling body 4 is made to have the initial speed V in this way, it is possible to allow the falling body 4 to reliably fall uniformly (reach the terminal falling speed) within a limited falling distance inside the measuring container 11.

<Measuring Sequence>

Figure 9:
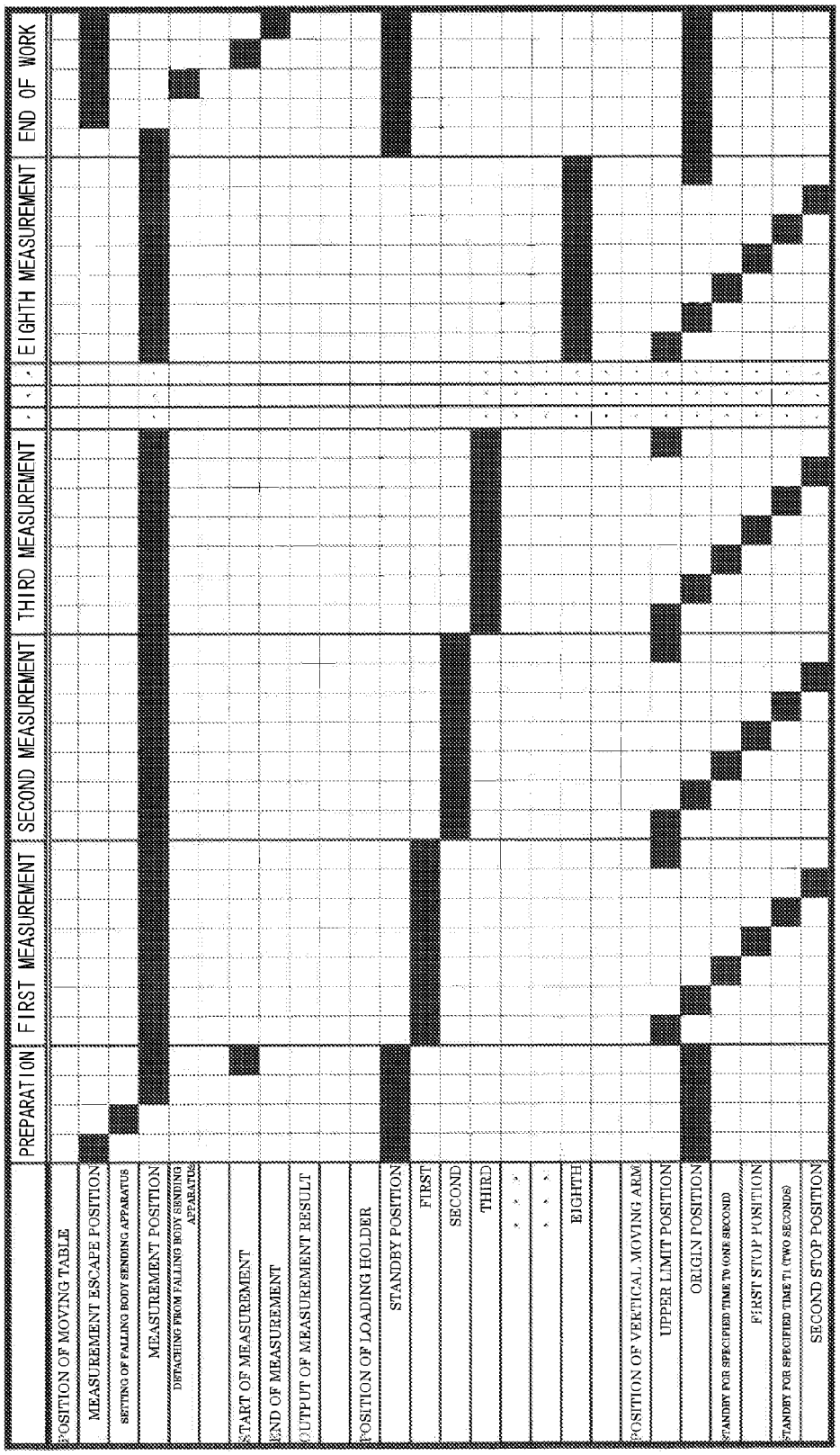
FIG. 9 is a diagram illustrating an automatic control for making the falling body sequentially fall.

With the above-described configuration, according to the time chart illustrated in FIG. 9, the viscosity of the measured substance may be measured by using plural falling bodies.

In this example, eight falling bodies in total continuously fall. Furthermore, eight falling bodies respectively have different densities (mg/cm$^3$). In this way, when the plural falling bodies with different densities are used, the Newtonian fluid/the non-Newtonian fluid to be described later may be determined.

According to the time chart of FIG. 9, the sequence will be described by referring to the configurations of FIGS. 1 to 8. First, as a preparation, as illustrated in FIG. 3, the moving table 22 is set to the measurement escape position 24, and the falling body sending apparatus 1 having the loading holder 13 and the measuring container 11 set therein is set in the outer cylinder 21. The moving table 22 is then moved to the measurement position 25.

Further, in this state, as illustrated in FIG. 1, the loading holder 13 is disposed at the standby position, and as illustrated in FIG. 7(b), the vertical moving arm 31 (the extruding pin 15) is disposed at the origin position 60. Then, as illustrated in FIG. 1, when the measurement is started in the operation-display device 10, the loading holder 13 slides leftward so that the loading unit 13a having the first falling body 4 which is disposed at the leftmost side of the drawing is disposed below the extruding pin 15. Further, as illustrated in FIGS. 6 and 7(b), the vertical moving arm 31 first moves up to the upper limit position 63 so as to adjust the zero point thereof, returns to the origin position 60, and then waits at the origin position 60 for a specified time T0 (in this example, for one second).

Next, as illustrated in FIGS. 7(b) and 8, the vertical moving arm 31 moves downward to the first stop position 61, and the lower portion of the falling body 4 protrudes from the guide portion 12c. This step is a first step.

Then, as illustrated in FIGS. 7(b) and 8, the standby state is continued at the first stop position 61 for the specified time T1 (in this example, for two seconds). The measured substance 3 infiltrates into the surface of the falling body 4 for the specified time T1. This step is a second step.

Subsequently, as illustrated in FIG. 7(c), the vertical moving arm 31 moves downward to the second stop position 62, so that the falling body 4 is sent into the measuring container 11. This step is a third step.

As described above, the method of sending the falling body includes following steps when sending the falling body 4 using the extruding pin 15: a first step (FIG. 7(a)) of attaching the measured substance 3 to the surface of the falling body 4 by setting a standby state in which a part of the falling body 4 advances into the measuring container 11; a second step (FIG. 7(b)) of maintaining the state of the falling body 4 in the first step for a specified time; and a third step (FIG. 7(c)) of sending the falling body 4 after the second step.

As described above, the first falling body is sent out, and as illustrated in FIG. 6, the vertical moving arm 31 moves upward so as to be returned to the upper limit position 63, so that the first measuring work is completed.

Next, as illustrated in FIG. 1, the loading holder 13 slides so that the loading unit 13a having the second falling body 4 from the leftmost side is disposed below the extruding pin 15, and then, the vertical moving arm is operated as in the case of the first measuring work.

As described above, the operations of the loading holder 13 and the extruding pin 15 (the vertical moving arm 31) illustrated in FIGS. 6 and 7 are repeated until the eighth measuring work is completed. Then, after the eighth measuring work is completed, the loading holder 13 is automatically returned to the standby position (the state of FIG. 1) of the preparation, and the vertical moving arm 31 is returned to the origin position 60. Subsequently, as illustrated in FIG. 3, the moving table 22 is returned from the measurement position 25 to the measurement escape position 24, and the falling body sending apparatus 1 is detached from the outer cylinder 21 to the upside thereof, thereby ending the measurement. After the measurement ends, the measurement result is outputted.

As described above, it is possible to automatically and continuously perform the measuring work with respect to the first to eighth falling bodies, reduce a work burden, or reduce a variation in the measurement result.

Furthermore, in the above-described example, as illustrated in FIG. 1, the loading holder 13 slides so as to sequentially drop the falling bodies. However, the extruding device 12 may slide without sliding the loading holder 13 so as to sequentially drop the falling bodies. That is, the relative position between the loading holder 13 and the extruding device 12 may be changed. In the case of the relative moving structure, the respective falling bodies may directly come into contact with the extruding pin 15, the respective falling bodies 4 may be sent out at the same condition, and then a variation in the measurement result may be reduced. Further, in the structure of changing the relative position, any movement instead of the sliding movement may be adopted. Further, the automatic measuring work which is described above may be automatically controlled by the arithmetic and control unit 9.

<Measurement of Falling Speed>

In the above-described configuration, the falling speed of the falling body may be measured in the falling speed measuring sensor 5 illustrated in FIG. 1. The falling speed measuring sensor 5 is not particularly limited, but as illustrated in FIG. 10, the falling speed may be calculated by analyzing a change in the potential generated in two coil pairs 91 and 92 disposed so as to surround the outer peripheral surface of the outer cylinder 21 (see FIG. 1) by using the arithmetic and control unit 9. More specifically, first, in the upper coil pair 91 (the first coil pair), coils 91a and 91b are disposed in parallel and are connected to each other so as to have different polarities, that is, opposite winding directions. Even in the lower coil pair 92 (the second coil pair), in the same way, coils 92a and 92b are disposed in parallel and are connected to each other so as to have different polarities.

Then, in the configuration of the falling speed measuring sensor 5 of FIG. 10, as illustrated in FIG. 11, the potential of each coil may be measured as a signal output (V). That is, when the falling body passes through the magnetic field of each coil, a change in the signal output (V) may be recorded through the induced electromotive force which is generated in each coil. Furthermore, in FIG. 11, the vertical axis indicates the signal output (V), and the horizontal axis indicates the time (t). Further, the horizontal axis also corresponds to the falling position of the falling body.

In FIG. 11, the waveform L1 illustrates the temporal change in the potential of the upper coil pair 91 (the coils 91a and 91b) of FIG. 10 through the signal output (V), and the waveform L2 illustrates the temporal change in the potential of the lower coil pair 92 (the coils 92a and 92b) of FIG. 10 through the signal output (V). With regard to the waveform L1, two extreme values M1 and M2 are illustrated and the first elapsed time Ta between the extreme values M1 and M2 is defined as a time which is necessary for the passage in the vertical center distance D1 of the coils 91a and 91b (the gap between the vertical center position of the coil 91a and the vertical center position of the coil 91b). In the same way, with regard to the waveform L2, two extreme values M3 and M4 are illustrated, and the second elapsed time Tb between the extreme values M3 and M4 is defined as a time which is necessary for the passage in the vertical center distance D2 of the coils 92a and 92b (the gap between the vertical center position of the coil 92a and the vertical center position of the coil 92b).

Then, with regard to the respective waveforms L1 and L2, for example, the falling speeds v1 and v2 of the falling body may be obtained by dividing the vertical center distances D1 and D2 by the first elapsed time Ta and the second elapsed time Tb (falling speed v1 (mm/msec)=D2 (mm)/Ta (msec) and falling speed v2 (mm/msec)=D2 (mm)/Ta (msec)). The average value of the falling speeds v1 and v2 may be defined as the falling speed, and any one of them may be adopted as a falling speed. Further, in addition, the time Tc between the intersection points M5 and M6 of the respective waveforms L1 and L2 and the reference potential V0 (the voltage which is applied to each coil in the power supply of the arithmetic and control unit 9) may be obtained, and the falling speed may be obtained from the time Tc.

Furthermore, in addition to the method of obtaining the falling speed using the waveforms L1 and L2 illustrated in FIG. 11 based on the configuration of the falling speed measuring sensor 5 illustrated in FIG. 10 and the configuration of FIG. 10, even in the method of connecting the coils of the coil pair illustrated in FIG. 10 in parallel to each other at the same polarities, two extreme values in each coil pair may be obtained, and the passage time of each coil may be obtained by using the extreme value. Accordingly, the method of winding the coil is not particularly limited.

Further, as the method of calculating the viscosity using the falling speed obtained as described above, the method which is disclosed in JP-A No. 8-219973 or JP-A No. 2006-208260 may be used, and when the method disclosed in such publications is executed by a program, the viscosity may be calculated.

<Determination of Type of Fluid>

Figure 12:
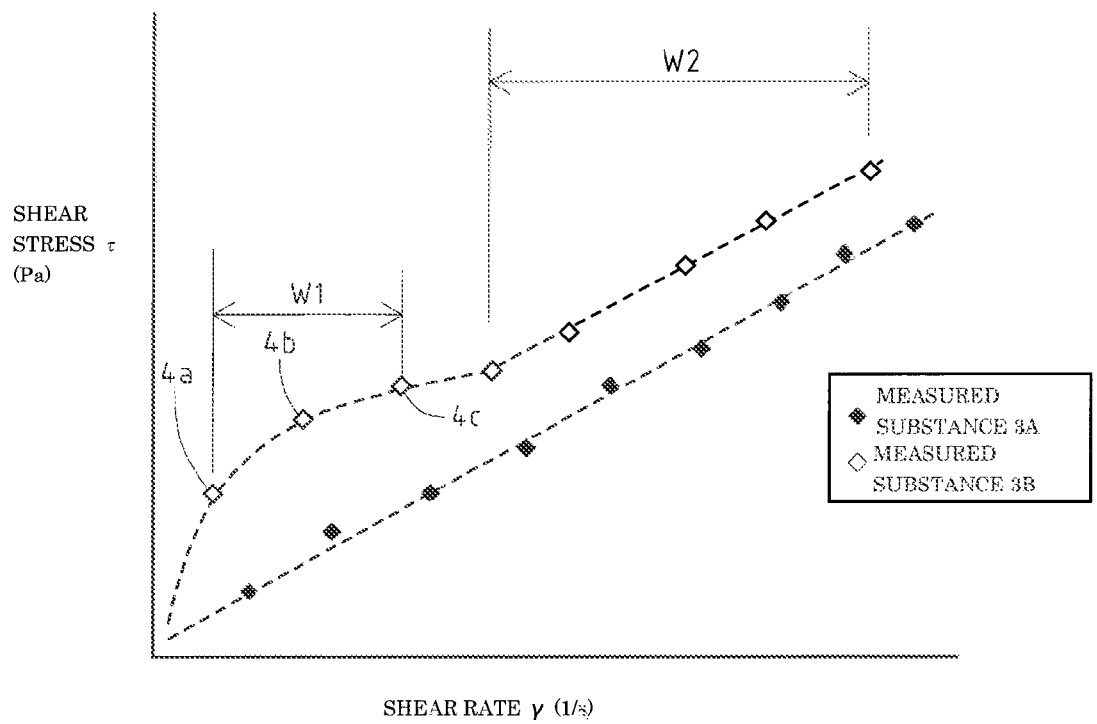
FIG. 12 is a diagram illustrating a relation between a shear rate and shear stress.

With regard to the calculation of the viscosity, as illustrated in FIG. 12, it is possible to determine whether the measured substance is a Newtonian fluid or a non-Newtonian fluid by plotting the shear rate γ (the horizontal axis (unit: 1/s (second)) and the shear stress τ (the vertical axis (unit: Pa)). That is, as in the above-described measurement example, the shear rate γ and the shear stress τ are obtained from eight falling bodies with different densities (mg/cm$^3$) based on the measurement values of the weight (mg) and the falling speed (m/s) and are plotted in the graph of FIG. 12. If the shear rate γ and the shear stress τ are proportional to each other so as to pass through the origins as in the measured substance 3A, it may be determined that the substance is a Newtonian fluid. On the other hand, if the proportional relation is not satisfied, that is, the shear rate γ and the shear stress τ are not proportional to each other so as to pass through the origins as in the measured substance 3B, it may be determined that the substance is a non-Newtonian fluid.

Further, according to the analysis in the graph of FIG. 12, the measured substance 3B moves like a Casson fluid in an area W1 where the weight (mg) (which may be the density (mg/cm$^3$)) of the falling body is small, and moves similarly to the Newtonian fluid in a linear (proportional) manner although it is not the Newtonian fluid because it does not pass through the origins in an area W2 where the weight (mg) of the falling body is large.

Furthermore, in the specification, the "Newtonian fluid" indicates that the shear rate and the shear stress are linear (proportional) to each other so as to pass through the origins in the graph illustrating the relation therebetween in FIG. 12. Further, the "non-Newtonian fluid" indicates a fluid except for the "Newtonian fluid".

<Determination of Falling State>

Further, in the above-described calculation of the viscosity of the measured substance, it is assumed that the falling body uniformly falls inside the measured substance, but in fact, there is a possibility that the falling body may not uniformly fall so that it cannot reach the terminal falling speed. In this case, because this may affect the graph of FIG. 12, there is a concern that the Newtonian fluid and the non-Newtonian fluid may be erroneously determined.

As for this, the falling state of the falling body may be determined by using the configuration of the falling speed measuring sensor 5 illustrated in FIG. 10 and the waveform illustrated in FIG. 11.

That is, as illustrated in FIG. 11, the falling state of the falling body is determined by comparing the first elapsed time Ta between two extreme values of one coil pair 91 and the second elapsed time Tb between two extreme values of the other coil pair 92.

In the waveform L1 of FIG. 11, when both the time Ta and the time Tb are approximately equal to each other, it takes the same time for the passage in the vertical center distances D1 and D2 (D1=D2) of the coil pairs 91 and 92 which are respectively set to the same distance, and hence it may be determined that the falling body falls uniformly. On the other hand, in the waveform L1, if the first elapsed time Ta for the upper coil pair 91 is larger than the second elapsed time Tb for the lower coil pair 92, it is considered that the speed of the falling body increases, and hence it may be determined that the falling body does not fall uniformly. Furthermore, in the waveform L1, if the first elapsed time Ta for the upper coil pair 91 is smaller than the second elapsed time Tb for the lower coil pair 92, it is considered that the speed of the falling body decreases, and hence it may be determined that the falling body does not fall uniformly.

The falling body does not fall uniformly because the falling body may be accelerated due to the low viscosity of the measured substance or the falling body may be decelerated due to the high viscosity. Further, it may be considered that the falling body falls uniformly in an area equal to or higher than a certain speed depending on the measured substance.

As described above, it is possible to determine the falling state such as whether the falling body falls uniformly or how the falling body falls (whether the falling body is accelerated or decelerated).

Further, if the falling body does not fall uniformly, as illustrated in FIG. 7(c), the vertical moving arm 31 (the extruding pin 15) applies the initial speed V to the falling body and adjusts the initial speed V, thereby performing an adjustment for allowing the falling body 4 to fall uniformly inside the measuring container 11. That is, the initial speed V is adjusted so that the first elapsed time Ta and the second elapsed time Tb are approximately equal to each other.

<Overall Sequence of Measuring Work: Example>

Figure 13:
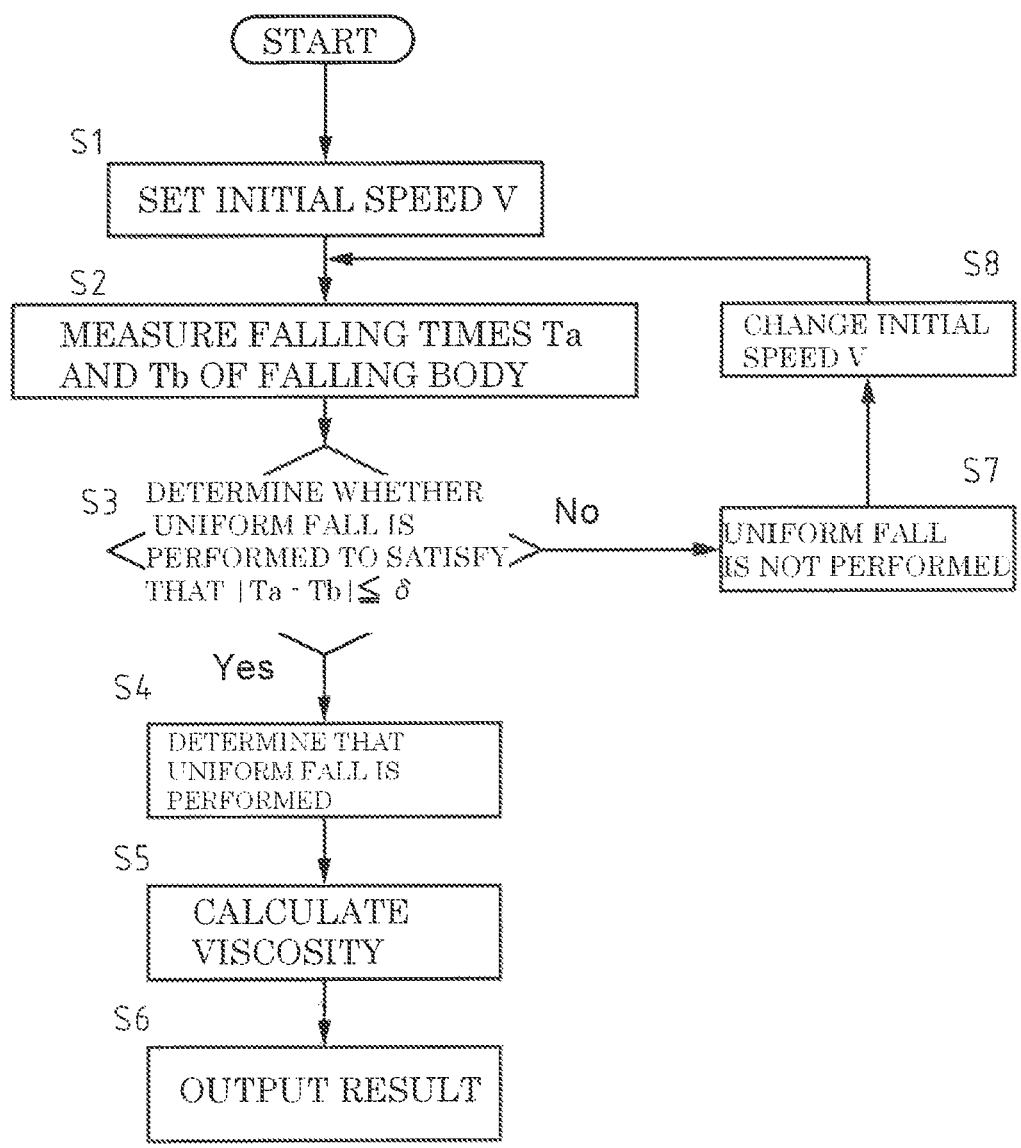
FIG. 13 is a flowchart illustrating an overall flow of a measuring work.

An example of a series of sequences when the falling speed or the viscosity of the falling body is measured or the type of the fluid is determined will be illustrated in the flowchart of FIG. 13.

According to the description using the flowchart, first, the initial speed V when the falling body falls is set (step S1), and the first elapsed time Ta and the second elapsed time Tb are measured (step S2). The measurement of the first elapsed time Ta and the second elapsed time Tb is automatically performed based on the above-described time chart (see FIG. 9). Next, in the arithmetic and control unit 9, the viscosity is calculated from the gradient (see FIG. 12) of the graph illustrating the relation between the shear rate and the shear stress for each falling body (step S5), and the result is output (step S6). According to this sequence, the viscosity may be calculated.

Further, in step S3 between step S2 and step S5, whether the falling body falls uniformly may be determined based on the measurement result of the first elapsed time Ta and the second elapsed time Tb. Here, with regard to the determination of the uniform falling, the reliability of the calculation result (the viscosity obtained in step S5) is low in the method of calculating the viscosity on the assumption that the falling body falls uniformly.

In step S3, the arithmetic and control unit 9 compares the first elapsed time Ta between two extreme values of one coil pair 91 with the second elapsed time Tb between two extreme values of the other coil pair 92 as illustrated in FIGS. 10 and 11. When the absolute value of the difference between both the time Ta and the time Tb is within the constant δ (the constant δ is a constant which is separately specified by the characteristic and the state of the measured substance or the characteristic of the apparatus), it is determined that the falling body falls uniformly (step S4), and the viscosity may be directly calculated (step S5).

On the other hand, in step S3, when the absolute value of the difference between both the time Ta and the time Tb is larger than the constant δ, it is determined that the falling body does not fall uniformly (step S7). One reason why the falling body does not fall uniformly is that the initial speed V may be low or high, and hence the initial speed V is changed (step S8). The initial speed V may be changed in a manner such that a measurer arbitrarily changes the initial speed V when the arithmetic and control unit 9 displays a demand for a change or the like on the operation-display device 10 or the arithmetic and control unit 9 automatically changes the initial value. The automatic change (adjustment) of the initial speed V using the arithmetic and control unit 9 may be repeated, for example, until both the time Ta and the time Tb are approximately equal to each other. Further, this operation may be performed as a preparation operation before the measurement starts.

By the above-described series of sequence, it is possible to usefully calculate the viscosity of the measured substance, determine the type of the fluid of the measured substance (the determination of the Newtonian fluid and the non-Newtonian fluid), and determine whether the falling body falls uniformly.

INDUSTRIAL APPLICABILITY

The invention may be used for the measurement of the viscosity of various substances such as blood, beverages, paint, chemicals, yeast, yogurt, mayonnaise, a resin, and the like through which the falling body may freely fall by the own weight. Further, the invention may be used for the measurement of the viscosity of not only the Newtonian fluid but also the non-Newtonian fluid.

The invention claimed is:

1. A method of determining a falling state of a falling body passing through a measured substance inserted into a measuring container by using a falling speed measuring sensor including a first coil pair which includes a pair of coils disposed in the outer periphery of the measuring container and separated from each other in the vertical direction and a second coil pair which includes a pair of coils disposed in the outer periphery of the measuring container, separated from each other in the vertical direction, and disposed below the first coil pair so as to be separated therefrom by a specified distance, the method comprising:
   measuring a first elapsed time which is a time interval between extreme values of two potentials generated in the first coil pair when the falling body passes through the first coil pair and a second elapsed time which is a time interval between extreme values of two potentials generated in the second coil pair when the falling body passes through the second coil pair; and
   determining the falling state of the falling body by comparing the first elapsed time with the second elapsed time.

2. A falling speed measuring sensor which measures a falling speed of a falling body passing through a measured substance inserted into a measuring container, the falling speed measuring sensor comprising:
   a first coil pair which includes a pair of coils disposed in the outer periphery of the measuring container and separated from each other in the vertical direction; and
   a second coil pair which includes a pair of coils disposed in the outer periphery of the measuring container, separated from each other in the vertical direction, and disposed below the first coil pair so as to be separated therefrom by a specified distance,
   wherein the falling speed measuring sensor is able to perform an operation of measuring a first elapsed time which is a time interval between extreme values of two potentials generated in the first coil pair when the falling body passes through the first coil pair and a second elapsed time which is a time interval between extreme values of two potentials generated in the second coil pair when the falling body passes through the second coil pair, and
   determining the falling state of the falling body by comparing the first elapsed time with the second elapsed time.

3. A falling body viscometer comprising:
   the falling speed measuring sensor according to claim 2.

4. A method of determining a falling state of a falling body passing through a measured substance inserted into a measuring container by using a falling speed measuring sensor including a first coil pair which includes a pair of coils disposed in the outer periphery of the measuring container and separated from each other in the vertical direction and a second coil pair which includes a pair of coils disposed in the outer periphery of the measuring container, separated from each other in the vertical direction, and disposed below the first coil pair so as to be separated therefrom by a specified distance, the method comprising:
   measuring a first elapsed time which is a time interval between extreme values of two potentials generated in the first coil pair when the falling body passes through the first coil pair and a second elapsed time which is a time interval between extreme values of two potentials generated in the second coil pair when the falling body passes through the second coil pair; and
   determining the falling state of the falling body in a manner such that a falling speed which is obtained by dividing the vertical center distance of the first coil pair by the first elapsed time is compared with a falling speed which is obtained by dividing the vertical center distance of the second coil pair by the second elapsed time.

5. A falling speed measuring sensor which measures a falling speed of a falling body passing through a measured substance inserted into a measuring container, the falling speed measuring sensor comprising:
   a first coil pair which includes a pair of coils disposed in the outer periphery of the measuring container and separated from each other in the vertical direction; and
   a second coil pair which includes a pair of coils disposed in the outer periphery of the measuring container, separated from each other in the vertical direction, and disposed below the first coil pair so as to be separated therefrom by a specified distance,
   wherein the falling speed measuring sensor is able to perform an operation of measuring a first elapsed time which is a time interval between extreme values of two potentials generated in the first coil pair when the falling body passes through the first coil pair and a second elapsed time which is a time interval between extreme values of two potentials generated in the second coil pair when the falling body passes through the second coil pair, and
   determining the falling state of the falling body in a manner such that a falling speed which is obtained by dividing the vertical center distance of the first coil pair by the first elapsed time is compared with a falling speed which is obtained by dividing the vertical center distance of the second coil pair by the second elapsed time.

6. A falling body viscometer comprising:
   the falling speed measuring sensor according to claim 5.

* * * * *